(12) United States Patent
Yang et al.

(10) Patent No.: US 7,286,632 B2
(45) Date of Patent: Oct. 23, 2007

(54) METHOD AND APPARATUS FOR MEASURING THE THICKNESS OF COMPRESSED OBJECTS

(75) Inventors: Jiwei Yang, North York (CA); Gordon Mawdsley, North York (CA); Martin Yaffe, Toronto (CA)

(73) Assignee: Sunnybrook and Women's College Health Sciences Ctr., Toronto, Ontario (CA)

( * ) Notice: Subject to any disclaimer, the term of this patent is extended or adjusted under 35 U.S.C. 154(b) by 256 days.

(21) Appl. No.: 10/517,325

(22) PCT Filed: Jun. 12, 2003

(86) PCT No.: PCT/CA03/00885

§ 371 (c)(1),
(2), (4) Date: Aug. 5, 2005

(87) PCT Pub. No.: WO04/000121

PCT Pub. Date: Dec. 31, 2003

(65) Prior Publication Data

US 2006/0034422 A1   Feb. 16, 2006

(30) Foreign Application Priority Data

Jun. 21, 2002   (CA) .................................... 2391133

(51) Int. Cl.
*A61B 6/04*   (2006.01)
(52) U.S. Cl. .............................. 378/37; 378/63; 378/164
(58) Field of Classification Search .................. 378/37, 378/63, 164
See application file for complete search history.

(56) References Cited

U.S. PATENT DOCUMENTS

| 4,515,165 | A | * | 5/1985 | Carroll ......................... 600/475 |
| 5,142,557 | A | | 8/1992 | Toker et al. |
| 5,260,985 | A | * | 11/1993 | Mosby ......................... 378/164 |
| 5,757,880 | A | * | 5/1998 | Colomb ......................... 378/37 |
| 6,198,838 | B1 | | 3/2001 | Roehrig et al. |

(Continued)

FOREIGN PATENT DOCUMENTS

EP    0 447 708 A2    11/1990

OTHER PUBLICATIONS

Burch A; Law J: "A method for estimating compressed breast thickness during mammography" The British Journal of Radiology, vol. 68, No. 808, Apr. 1995, pp. 394-399, XP008022400 England.

(Continued)

*Primary Examiner*—Edward J. Glick
*Assistant Examiner*—Thomas R. Artman
(74) *Attorney, Agent, or Firm*—Bereskin & Parr (57) ABSTRACT

A method and apparatus for determining a degree of deflection in a breast compression plate. The mammography apparatus further includes an optical measuring device. The method and apparatus involve (a) providing a pattern on the breast compression plate, the pattern being imagable by the optical measuring device, and having a plurality of local pattern indicia; (b) adjusting the breast compression plate to a selected height; (c) imaging the breast compression plate using the optical measuring device to provide an image of the pattern, the image having a plurality of local image indicia including an associated local image indicia for each local pattern indicia in the plurality of local pattern indicia; and (d) for each local pattern indicia in the plurality of local pattern indicia, determining an associated local deflection of the breast compression plate from the associated local image indicia.

9 Claims, 5 Drawing Sheets

U.S. PATENT DOCUMENTS

| | | | |
|---|---|---|---|
| 6,242,926 B1 | 6/2001 | Gardopee et al. | |
| 6,674,835 B2* | 1/2004 | Kaufhold et al. | 378/53 |
| 7,092,482 B2* | 8/2006 | Besson | 378/37 |
| 2002/0057832 A1 | 5/2002 | Oosterlinck et al. | |

OTHER PUBLICATIONS

Law, J. editor: "The commissioning and Routine Testing of Mammographic X-ray System", Institute of Physical Sciences in Medicine, York UK, (1994) Report 89, 56-86.

Dance, D.R.: Monte Carlo Calculation of Conversion Factors for the Estimation of Mean Glandular Breast Dose; Phys. Med. Biol, 1990, vol. 35, 1211-1219, UK.

McParland, B.J., PhD, Fipem and Boyd M.M. MSc: "A Comparison of Fixed and Variable kVp Technique Protocols for Film-Screen Mammography"—The British Journal of Radiology, (Jun. 2000), 613-626.

* cited by examiner

METHOD AND APPARATUS FOR MEASURING THE THICKNESS OF COMPRESSED OBJECTS

FIELD OF THE INVENTION

This invention relates in general to a method and apparatus for measuring the thickness of compressed objects, and more specifically relates to a method and apparatus for determining the degree of deflection of a breast compression plate in a mammography apparatus.

BACKGROUND OF THE INVENTION

In conventional mammography, a woman places her breast on a breast support plate. A detector is typically mounted under the breast support plate. This detector is sensitive to x-rays. A breast compressor plate that is transparent to light and x-rays presses against the top of the breast to flatten it and to prevent any movement during the mammography process. An x-ray source is then turned on to image the breast, which is between the breast support plate and the breast compression plate.

The transmitted x-ray intensity through the breast is dependent on both the composition of the breast and its local thickness. Most current mammography machines have thickness indicators, which are imprecise. These thickness indicators do not show true breast thickness if either the breast support plate or the compression plate bend or flex. This, in turn, will affect the accuracy and precision of the images of the breast obtained.

Techniques for determining the degree of flex of the breast compression plate have been devised. For example, see Burch, A. and Law, J., *A Method for Estimating Compressed Breast Thickness During Mammography*. Br J Radiol 68, (1995) 394-399, which discloses using the magnification of lead markers placed on top of the compression plate. However, this method requires that all the markers be shown in the image, and does not measure the flexing of plastic plates.

Accurate measurement of compressed breast thickness is an important factor in determining volumetric breast density. It is also an important factor in determining dose calculation (for example, Wu. X., Gingold E. L. Barnes G. T., Tucker D m Normalized average glandular dose in Mo/Rh and Rh/Rh target-filter mammography radiology 1994 193 at 83 to 89; Law, J., editor: *The Commissioning and Routine Testing of Mammographic X-ray System*, Institute of Physical Sciences in Medicine, York UK, (1994) 59; Dance, D. R.: *Monte Carlo Calculation of Conversion Factors for the Estimation of Mean Glandular Breast Dose*, Phy Med Biol, 35, (1990) 1211-1219. The measurement of actual thickness provided by commercial mammography can be as much as one centimeter off the actual thickness due to deflection of the breast compression plate.

Accordingly, a mammography apparatus and method that improves the accuracy of measuring breast thickness is desirable.

SUMMARY OF THE INVENTION

An object of an aspect of the present invention is to provide an improved method of determining a degree of deflection in a breast compression plate.

In accordance with an aspect of the present invention, there is provided a method of determining a degree of deflection in a breast compression plate of a mammography apparatus. The mammography apparatus further includes an optical measuring device. The method comprises: (a) providing a pattern on the breast compression plate, the pattern being imagable by the optical measuring device, and having a plurality of local pattern indicia; (b) adjusting the breast compression plate to a selected height; (c) imaging the breast compression plate using the optical measuring device to provide an image of the pattern, the image having a plurality of local image indicia including an associated local image indicia for each local pattern indicia in the plurality of local pattern indicia; and (d) for each local pattern indicia in the plurality of local pattern indicia, determining an associated local deflection of the breast compression plate from the associated local image indicia.

An object of a further aspect of the present invention is to provide an improved mammography apparatus for imaging breasts.

In accordance with a further aspect of the present invention, there is provided an apparatus comprising (a) a breast compression plate for compressing a breast to be imaged, the breast compression plate having a vertical adjustment means for adjusting the height of the breast compression plate to a selected height, and an optically-readable pattern; (b) a breast imaging means for imaging the breast compressed by the compression plate; (c) an optical measurement means for generating an image of the optically-readable pattern; and, (d) calculating means for determining a deflection of the breast compression plate from the selected height from the image of the optically readable pattern.

BRIEF DESCRIPTION OF THE DRAWINGS

A detailed description of preferred aspects of the invention is provided herein below with reference to the following drawings, in which.

DETAILED DESCRIPTION OF THE PREFERRED EMBODIMENTS OF THE INVENTION

Figure 1:
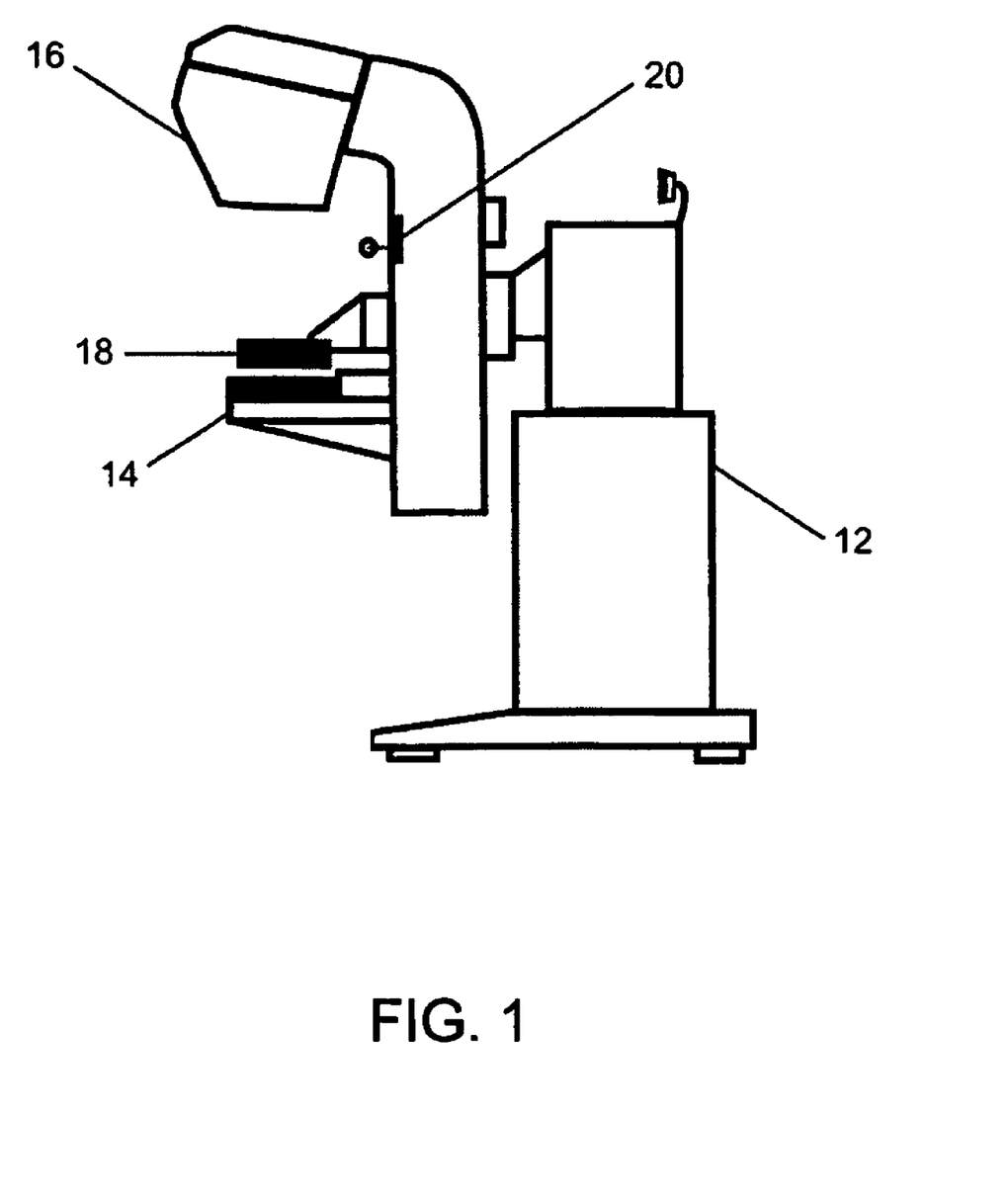
FIG. 1, in a perspective view, illustrates a mammography machine in accordance with the preferred embodiment of the present invention.

Referring to FIG. 1, there is illustrated in a perspective view, a mammography machine 12. The mammography machine 12 includes a breast support plate 14, a breast compression plate 18, an x-ray tube 16 and a camera 20. In operation, the x-ray tube 16 projects x-rays through the breast compression plate 18, which is transparent to light and x-rays, through the breast, and through the breast support plate 14. The breast compression plate 18 may be vertically adjusted to accommodate breasts of different dimensions. The breast support plate 14 includes a detector (not shown) that is sensitive to the x-rays. Variation in the density of the breast will have an effect on the x-rays traveling through the breast, which will affect the image left on the detector in the breast support plate 14. These signal variations may then be examined for possible tumors or other conditions. As discussed above, the transmitted x-ray intensity through the breast depends both on the composition of the breast and the thickness of the breast. Accordingly, to properly interpret the image, the thickness of the breast must be known. To accurately know the thickness of the breast, the deflection of the breast compression plate 18 must also be known. Deflection of the breast support plate 14 is much less of a concern, as this plate is comparatively rigid.

Figure 2:
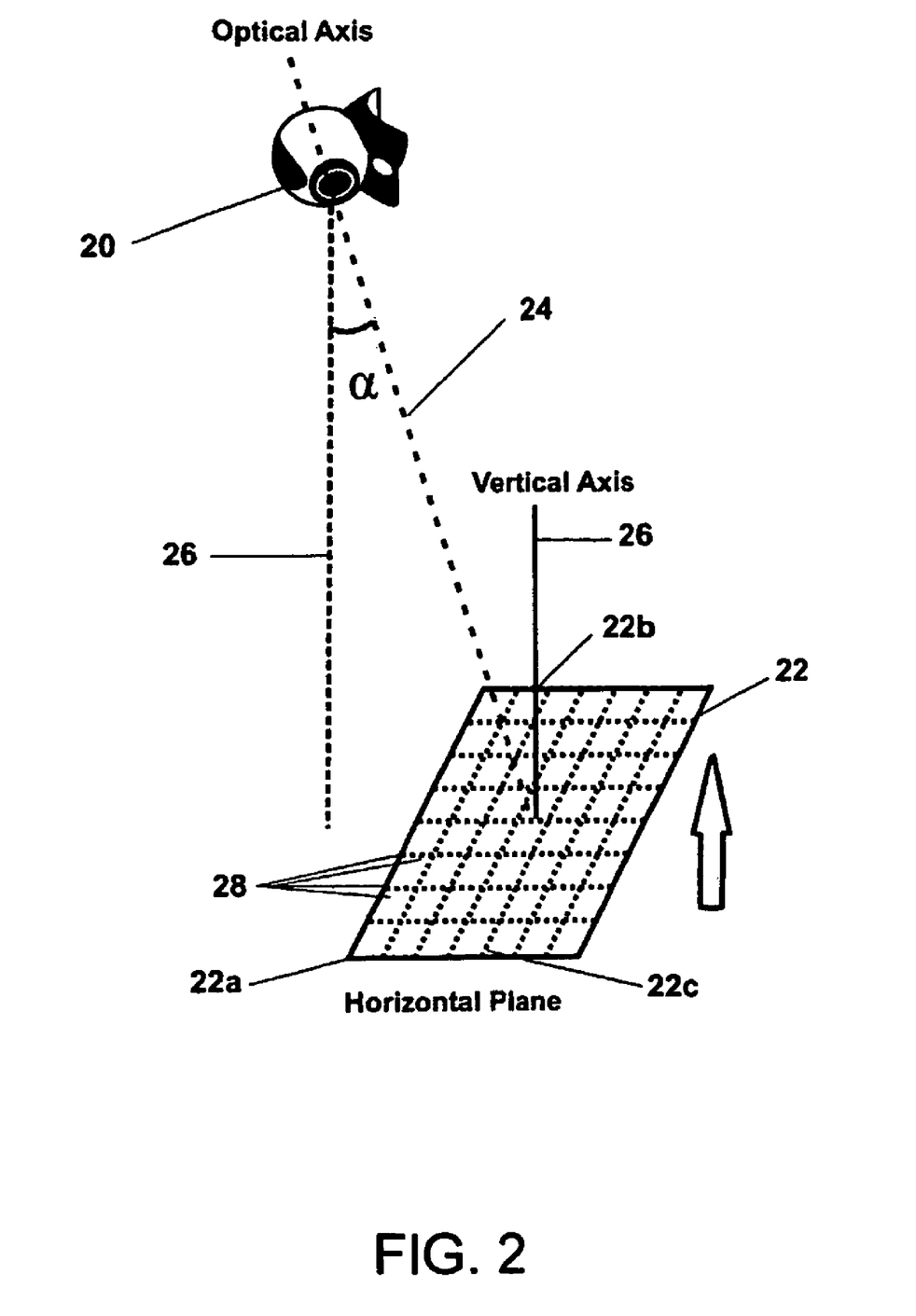
FIG. 2 is a schematic drawing showing the optical axis of a CCD (Charge-Coupled Device) camera, and the orientation of this optical axis relative to a horizontal plane having a grid-like pattern.

According to an embodiment of the present invention, a grid-like pattern is provided on the top of the breast compression plate 18. Referring to FIG. 2, the orientation of this camera 20 is shown relative to a grid-like pattern 22 on the upper side of breast compression plate 18. The camera 20 has an optical axis 24 that forms an angle $\alpha$ relative to the vertical axis 26 normal to the horizontal plane of the breast compression plate 18 bearing the grid-like pattern 22. As will be apparent to those skilled in the art, when the grid-like pattern 22 is moved up or down the vertical axis, this will change the image of each intersection point 28 generated by the camera 20. This is illustrated in more detail in FIG. 3 with respect to one square of the grid-like pattern 22, and specifically with respect to point $28_0$.

Figure 3:
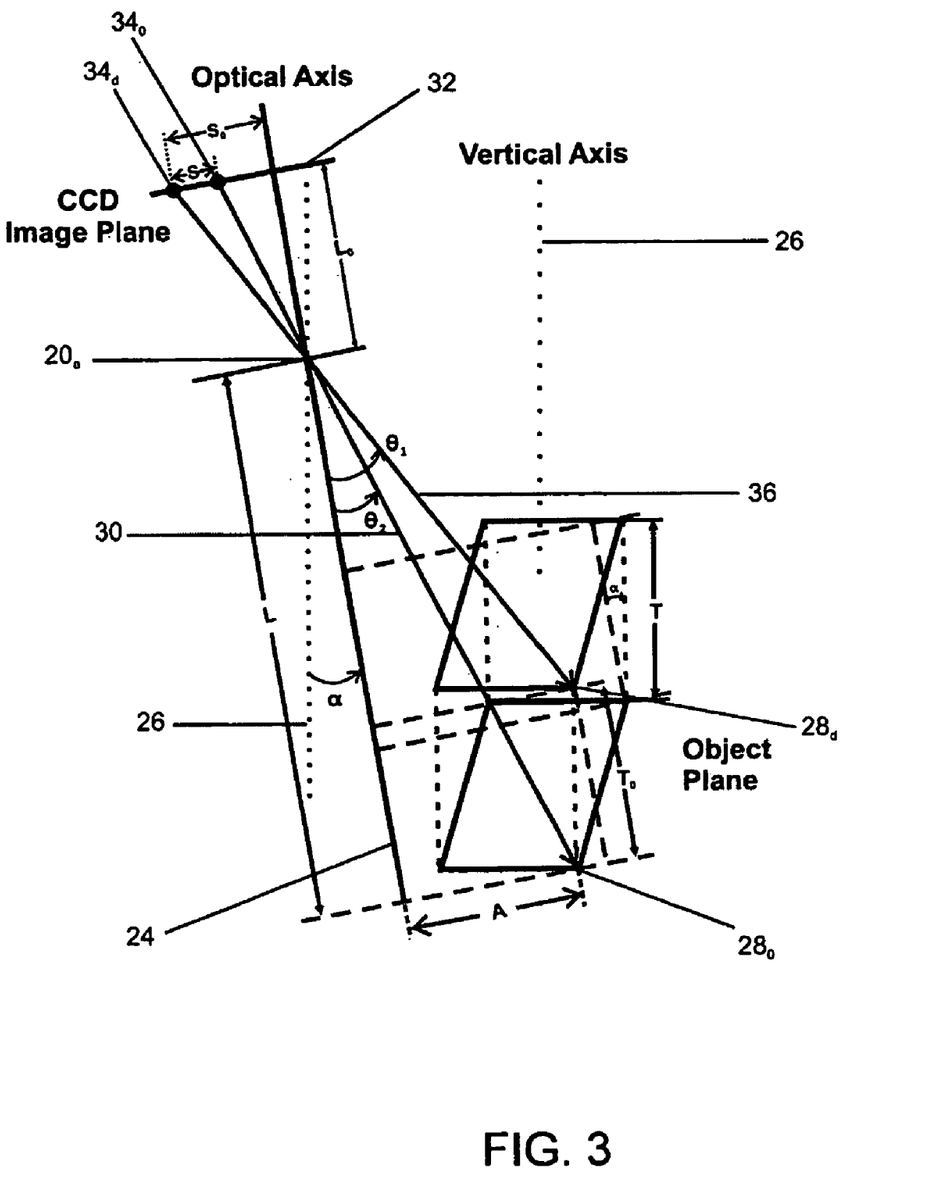
FIG. 3, in a schematic view, illustrates the optical pattern of one of these squares of the pattern of the horizontal plane of FIG. 2.

Referring to FIG. 3, there is illustrated in a not-to-scale schematic view, how the image on the camera changes based on flexion or other vertical movement of the breast compression plate 18. The location of the lens of the camera 20 is marked 20a in FIG. 3. A line of sight 30 connects intersection point $28_0$ with lens location 20a. This line 30 is then extended to an image plane 32. The intersection of the line 30 with the image plane 32 marks the image point $34_0$ corresponding to intersection point $28_0$. The intersection point $28_0$ is displaced from the optical axis by an initial distance A. The angle between line of sight 30 and optical axis 24 is $\theta_2$.

Say that the breast compression plate 18 is flexed upwardly by a breast compressed between the breast compression plate 18 and the breast support plate 14. This upward displacement will vary from intersection point 28 to other intersection points 28 based on fluctuation in breast thickness and compressibility. However, for the particular intersection point $28_0$ with which FIG. 3 is concerned, the deflection is by an amount T in a direction normal to the horizontal plane of the breast compression plate 18. As a result of the deflection of intersection point $28_0$ to a new position shown as $28_d$, a new line of sight 36 to the lens position 20a is generated. When extended back to the image plane 32, this line of sight 36 intersects at new image point $34_d$. This new image point $34_d$ is a shift S from the initial image point $34_0$ and is displaced from the optical axis 27 by a distance $S_0$. Line of sight 36 is at an angle $\theta_1$ to optical axis 24.

As shown in the drawing, the lens position 20a is defined by angle $\alpha$, as well as by distances L and $L_0$, both of which distances are measured parallel to the optical axis 24. Distance L is the distance from the camera lens 20a to the plane of the displacement point $28_0$. $L_0$ is the distance from the camera lens 20a to the image plane 32. The parameters $T_0$, $S_0$ and $\theta_2$ are fixed relative to each intersection point 28, although these parameters change for different intersection points 28. The parameters $\theta_1$, S and T change depending on the degree of flexing of the breast compression plate. However, as shown below, the thickness T varies linearly with the shift S.

From trigonometry, $\tan(\theta_2)=A/L=(S_0-S)/L_0$ and $\tan(\theta_1)= [A+T_0*\tan(\alpha)]/(L-T_0)=S_0/L_0$ $$A/L=(S_0-S)/L_0 \quad (1)$$

and $$[A+T_0*\tan(\alpha)]/(L-T_0)=S_0/L_0 \quad (2)$$

Finally, based on trigonometry and then solving for $T_0$ using equations (1) and (2)

$$T=T_0/\cos\alpha=S(L/L_0)[S_0\cos\alpha/L_0+\sin\alpha] \quad (3)$$

Figure 4:
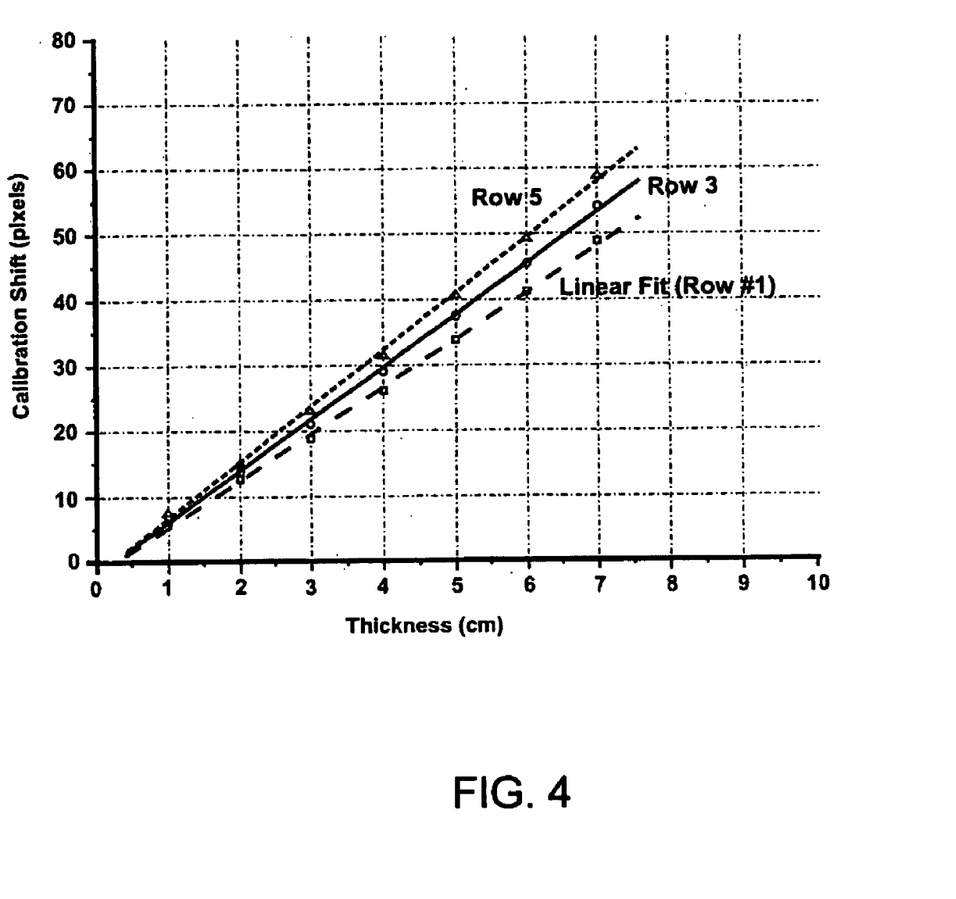
FIG. 4, in a graph, plots the pattern shift of different rows of the grid pattern of FIG. 2 against thickness; and, FIG. 5 in a three-dimensional graph, plots thickness in centimeters against grid column and row location.

These results were also verified empirically by changing the position of the breast compression plate. The shift of grid marks on the image plate was then mapped as a linear function of the height of the breast compression plate 18 for each X, Y coordinate of the grid pattern. Referring to FIG. 4, the relative shift for intersection points 28 in a first row 22a, a third row 22b and a fifth row 22c of the grid pattern 22 are shown. Clearly, $\theta_2$ increases with the horizontal distance from the camera such that for the fifth row 22c $\theta_2$ is larger than $\theta_2$ is for the first row 22a. $\theta_2$ for the third row 22b is smaller than $\theta_2$ for the fifth row 22c, and is larger than $\theta_2$ for the first row 22a. As a result, the shift S for intersection points 28 in the fifth row 22c will be greater than the shift S for intersection points 28 in the first row 22a. However, in both cases there is a linear relation between the shift S and the thickness T. This is clearly reflected in the lines plotted in the graph of FIG. 4. Accordingly, the thickness at an individual intersection point 28 can be computed from an image of the grid pattern 22 taken along with each mammographic study.

Figure 5:
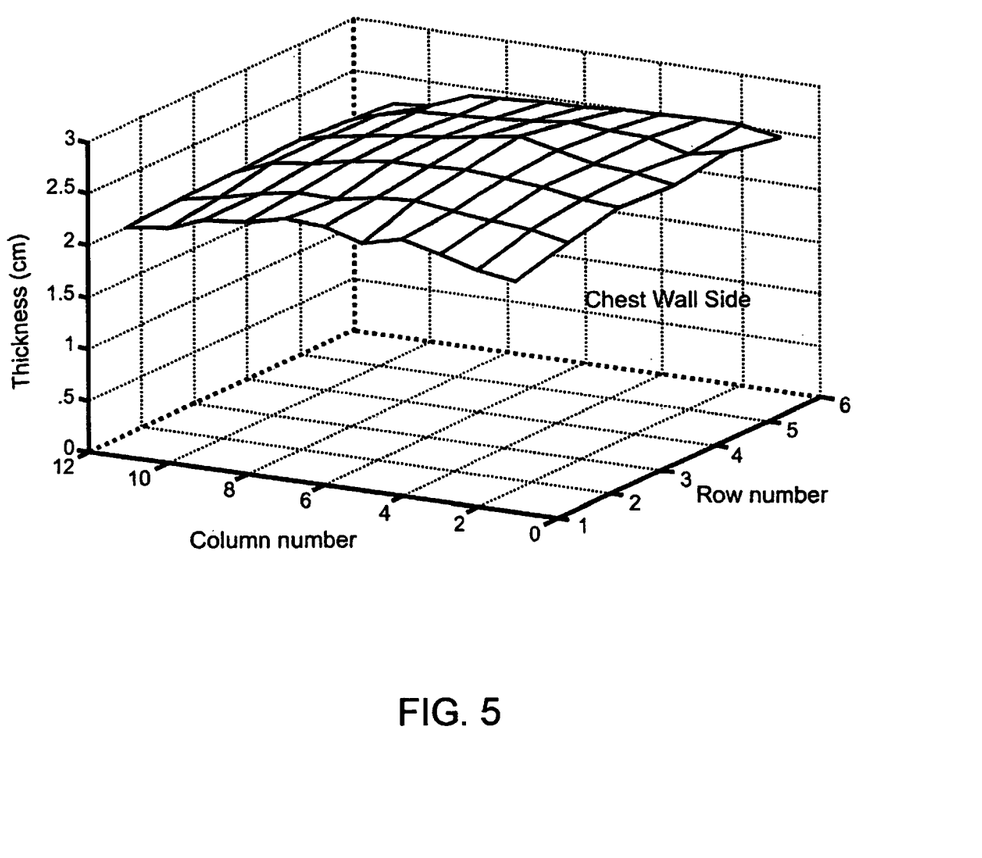

Referring to FIG. 5, there is illustrated in a three-dimensional graph, a thickness map. The thickness map plots the displacement between the breast compression plate 18 and the breast support plate 14 at different X and Y positions on the grid. This displacement can be determined from the image of the grid at these X and Y positions in accordance with the above-described method.

Other variations and modifications of the invention are possible. For example, other non-grid patterns may be provided on the top of the breast compression plate to enable its deflection to be determined. All such applications, modifications or variations are believed to be within the sphere and scope of the invention as defined by the claims appended hereto.

The invention claimed is:

1. A method of determining a degree of deflection in a breast compression plate of a mammography apparatus, the mammography apparatus further including an optical measuring device, the method comprising:
    (a) providing a pattern on the breast compression plate, the pattern being imagable by the optical measuring device, and having a plurality of local pattern indicia;
    (b) adjusting the breast compression plate to a selected height;
    (c) imaging the breast compression plate using the optical measuring device to provide an image of the pattern, the image having a plurality of local image indicia including an associated local image indicia for each local pattern indicia in the plurality of local pattern indicia; and
    (d) for each local pattern indicia in the plurality of local pattern indicia, determining an associated local deflection of the breast compression plate from the associated local image indicia.

2. The method as defined in claim 1 wherein the breast support plate is adjustable, the method further comprising moving the breast support plate to a plurality of different positions; and for each position in the plurality of different positions, determining a position-specific image of the pattern, the position-specific image including an associated position-specific local image indicia for each local pattern indicia at each position in the plurality of positions;

wherein step (c) comprises, for each local pattern indicia in the plurality of local pattern indicia, determining the associated local deflection of the breast support plate by correlating the associated degree of shift in the associated local image indicia with an associated position-specific local image indicia.

3. The method as defined in claim 1 wherein the pattern is a two-dimensional radio-lucent pattern.

4. The method as defined in claim 3 wherein the pattern is a grid, and each local pattern indicia is a point on the grid.

5. The method as defined in claim 2 wherein the step of determining a position-specific image of the pattern for each position in the plurality of different positions, comprises imaging the breast support plate at each different position using the optical measuring device to provide the position-specific image of the pattern.

6. A mammography apparatus for imaging breasts, the apparatus comprising a breast compression plate for compressing a breast to be imaged, the breast compression plate having a vertical adjustment means for adjusting the height of the breast compression plate to a selected height, and an optically-readable pattern;

a breast imaging means for imaging the breast compressed by the compression plate;

an optical measurement means for generating an image of the optically-readable pattern; and, calculating means for determining a deflection of the breast compression plate from the selected height from the image of the optically readable pattern.

7. The mammography machine as defined in claim 6 wherein the pattern has a plurality of local pattern indicia;

the image has a plurality of local image indicia including an associated local image indicia for each local pattern indicia in the plurality of local pattern indicia; and for each local pattern indicia in the plurality of local pattern indicia, the data processing means is operable to determine an associated local deflection of the breast compression plate from the associated local image indicia.

8. The method as defined in claim 6 wherein the pattern is a two-dimensional radio-lucent pattern.

9. The method as defined in claim 6 wherein the pattern is a grid, and each local pattern indicia is a point on the grid.

* * * * *

UNITED STATES PATENT AND TRADEMARK OFFICE
CERTIFICATE OF CORRECTION

PATENT NO. : 7,286,632 B2  Page 1 of 1
APPLICATION NO. : 10/517325
DATED : October 23, 2007
INVENTOR(S) : Jiwei Yang, Gordon Mawdsley and Martin Yaffe It is certified that error appears in the above-identified patent and that said Letters Patent is hereby corrected as shown below:

Column 5, claim 2, lines 1-2, "the breast support plate" should be changed to --a breast support plate--.

Column 6, claim 7, line 12, "mammography machine" should be changed to --mammography apparatus--; line 20, "the data processing means" should be changed to --a data processing means--.

Column 6, claim 8, line 25, "method" should be changed to --apparatus--.

Column 6, claim 9, line 27, "method" should be changed to --apparatus--.

Signed and Sealed this

Ninth Day of November, 2010

David J. Kappos
*Director of the United States Patent and Trademark Office*